(12) United States Patent
Cooper et al.

(10) Patent No.: US 11,065,271 B2
(45) Date of Patent: Jul. 20, 2021

(54) MATERNAL VITAMIN B12 ADMINISTRATION FOR THE PREVENTION OF INCREASED ADIPOSITY, OVERWEIGHT OR OBESITY IN THE OFFSPRING ESPECIALLY OFFSPRING OVERWEIGHT AND/OR OBESE MOTHERS

(71) Applicant: Société des Produits Nestlé S.A., Vevey (CH)

(72) Inventors: Cyrus Cooper, Southampton Hampshire (GB); Peter David Gluckman, Auckland (NZ); Irma Silva Zolezzi, Carrouge (CH); Keith Malcolm Godfrey, Ashurst Hampshire (GB); Catherine Mace, Lausanne (CH)

(73) Assignee: Societe des Produits Nestle S.A., Vevey (CH)

(*) Notice: Subject to any disclaimer, the term of this patent is extended or adjusted under 35 U.S.C. 154(b) by 0 days.

(21) Appl. No.: 16/681,398

(22) Filed: Nov. 12, 2019

(65) Prior Publication Data
US 2020/0188421 A1 Jun. 18, 2020

Related U.S. Application Data

(62) Division of application No. 15/107,570, filed as application No. PCT/EP2015/050360 on Jan. 9, 2015, now Pat. No. 10,517,891.

(30) Foreign Application Priority Data

Jan. 10, 2014 (EP) .................................. 14150793
Mar. 21, 2014 (EP) .................................. 14161184

(51) Int. Cl.
*A61K 35/741* (2015.01)
*A61K 31/714* (2006.01)
(Continued)

(52) U.S. Cl.
CPC ............ *A61K 31/714* (2013.01); *A23L 33/15* (2016.08); *A23L 33/30* (2016.08); *A23L 33/40* (2016.08);
(Continued)

(58) Field of Classification Search
CPC ..................................................... A61K 35/741
See application file for complete search history.

(56) References Cited

U.S. PATENT DOCUMENTS 5,494,678 A 2/1996 Paradissis et al.
2006/0280840 A1* 12/2006 Robertson ............. A23L 33/185
426/72

(Continued)

FOREIGN PATENT DOCUMENTS

| CN | 103478261 | 1/2014 |
| EP | 2147678 | 1/2010 |

(Continued)

OTHER PUBLICATIONS

"Dietary Reference Intakes for Thiamin, Riboflavin, Niacin, Vitamin B6, Folate, Vitamin B12, Pantothenic Acid, Biotin, and Choline", National Academy Press, 1998, 592 pages.

(Continued)

*Primary Examiner* — Rosanne Kosson
(74) *Attorney, Agent, or Firm* — K&L Gates LLP

(57) ABSTRACT

The present invention generally relates to the early prevention of overweight, obesity, excessive fat accumulation and/or associated metabolic disorders in infants or children. For example, the present invention relates to the prevention of over-weight, obesity, excessive fat accumulation and/or associated metabolic disorders in infants or children through appropriate nutrition for women desiring to get pregnant and/or during pregnancy and/or lactation. Embodiments of the present invention relate to vitamin B12 for use in the (Continued)

prevention of overweight, obesity, excessive fat accumulation and/or associated metabolic disorders in the off-spring, wherein the vitamin B12 is administered to an overweight and/or obese women desiring to get pregnant and/or to the over-weight and/or obese mother during pregnancy and/or lactation and to maternal food compositions that can be used for this purpose.

5 Claims, 1 Drawing Sheet

(51) Int. Cl.
    *A23L 33/15* (2016.01)
    *A23L 33/00* (2016.01)
    *A61K 9/00* (2006.01)
    *A61K 45/06* (2006.01)
(52) U.S. Cl.
    CPC ............ *A61K 9/0095* (2013.01); *A61K 45/06* (2013.01); *A23V 2002/00* (2013.01)

(56) References Cited

U.S. PATENT DOCUMENTS

| | | | |
|---|---|---|---|
| 2007/0054358 | A1 | 3/2007 | Blattner et al. |
| 2008/0187606 | A1 | 8/2008 | Kim et al. |
| 2010/0111915 | A1 | 5/2010 | Isolauri et al. |
| 2012/0027897 | A1 | 2/2012 | Innocenzi |

FOREIGN PATENT DOCUMENTS

| | | |
|---|---|---|
| WO | 9963943 | 12/1999 |
| WO | 2007135141 | 11/2007 |

OTHER PUBLICATIONS

Carmel, "How I Treat Cobalamin (Vitamin B12) Deficiency", Blood, vol. 112, Issue No. 6, Sep. 15, 2008, pp. 2214-2221.
Yazaki et al., "A Single-Center, Double-Blinded, Randomized Controlled Study to Evaluate the Relative Efficacy of Sublingual and Oral Vitamin B-Complex Administration in Reducing Total Serum Homocysteine Levels", The Journal of Alternative and Complementary Medicine, vol. 12, Issue No. 9, Nov. 16, 2006, pp. 881-885.
Sharabi et al., "Replacement Therapy for Vitamin B12 Deficiency: Comparison Between the Sublingual and Oral Route", British Journal of Clinical Pharmacology, vol. 56, Nov. 14, 2003, pp. 635-638.
Philippines Communication for Invention 1/2016/500915 dated Nov. 29, 2019.
Krishnaveni et al. "Low plasma vitamin B12 in pregnancy is associated with gestational 'diabesity' and later diabetes" Diabetologia, 2009, vol. 52, pp. 2350-2358.
Stewart et al. "Low Maternal Vitamin B-12 Status Is Associated with Offspring Insulin Resistance Regardless of Antenatal Micronutrient Supplementation in Rural Nepal1,2" Yhe Journal of Nutrition, 2011, vol. 141, pp. 1912-1917.
Yajnik et al. "Vitamin B12 and folate concentrations during pregnancy and insulin resistance in the offspring: the Pune Maternal Nutrition Study" Diabetologia, 2008, vol. 51, pp. 29-38.
Ciappio et al. "Maternal one-carbon nutrient intake and cancer risk in offspring" Nutrition Reviews, 2011, vol. 69, No. 10, pp. 561-571.
Ruager-Martin et al. "Maternal obesity and infant outcomes" Early Human Development, 2010, vol. 86, pp. 715-722.
Kumar et al. "Maternal dietary folate and/or vitamin B12 restrictions alter body composition (adiposity) and lipid metabolism in Wistar rat offspring" Journal of Nutritional Biochemistry, 2013, vol. 24, pp. 25-31.
Russian Office Action for corresponding Russian Application No. 2016132886, dated Sep. 6, 2018 (12 pages).

* cited by examiner

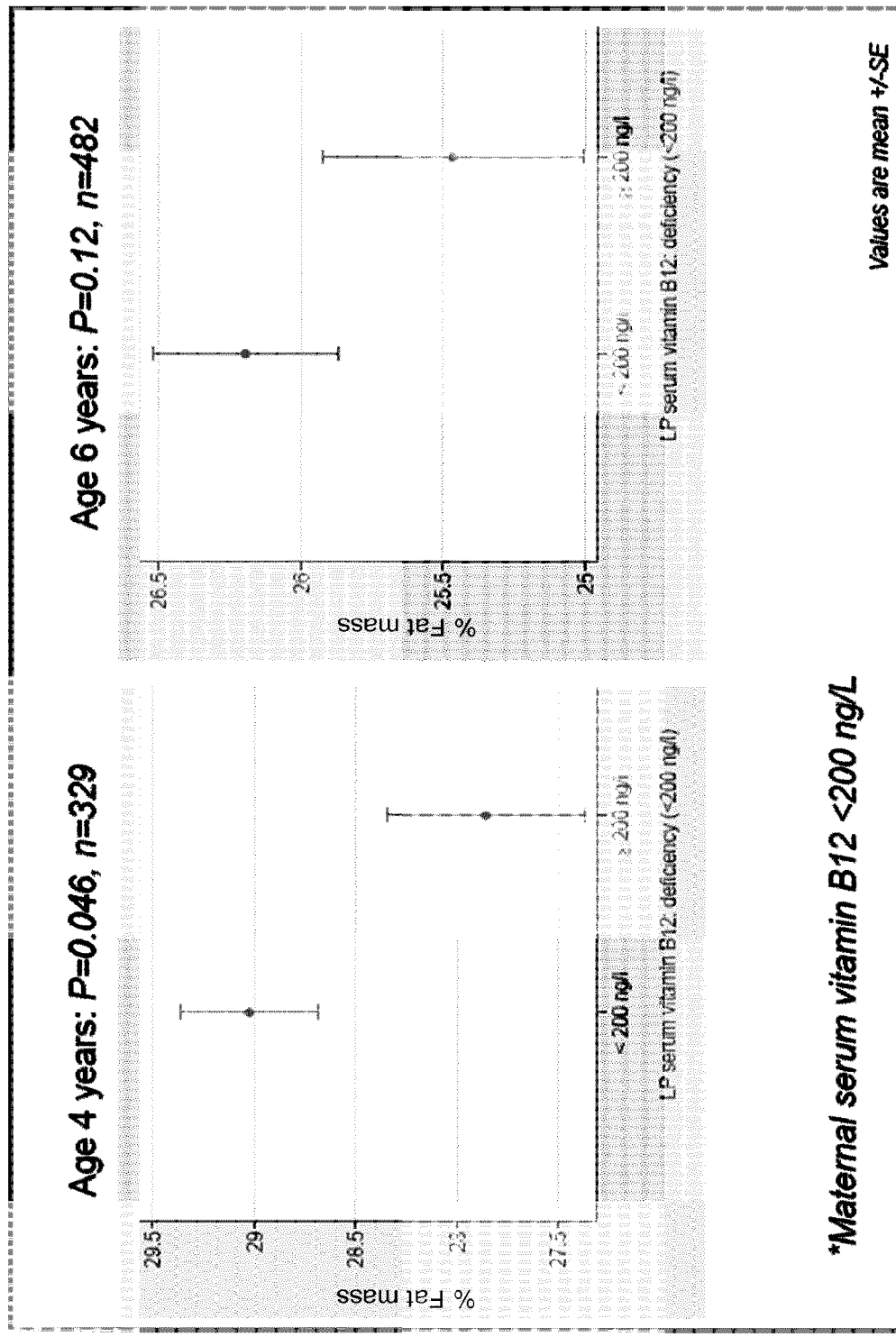

MATERNAL VITAMIN B12 ADMINISTRATION FOR THE PREVENTION OF INCREASED ADIPOSITY, OVERWEIGHT OR OBESITY IN THE OFFSPRING ESPECIALLY OFFSPRING OVERWEIGHT AND/OR OBESE MOTHERS

PRIORITY CLAIMS

This application is a divisional of U.S. application Ser. No. 15/107,570 filed Jun. 23, 2016, which is a National Stage of International Application No. PCT/EP15/50360 filed Jan. 9, 2015, which claims priority to European Patent Application No. 14150793.9 filed Jan. 10, 2014 and European Patent Application No. 14161184.8 filed Mar. 21, 2014, the entire contents of which are incorporated herein by reference.

FIELD OF THE INVENTION

The present invention generally relates to the early prevention of overweight, obesity, excessive fat accumulation and/or associated metabolic disorders in infants or children. For example, the present invention relates to the prevention of overweight, obesity, excessive fat accumulation and/or associated metabolic disorders in infants or children through appropriate maternal nutrition before pregnancy, during pregnancy and/or during lactation. Embodiments of the present invention relate to vitamin B12 for use in the prevention of overweight, obesity, excessive fat accumulation and/or associated metabolic disorders in the offspring, wherein the vitamin B12 is administered to an overweight and/or obese mother before pregnancy, during pregnancy and/or during lactation and to maternal food compositions that can be used for this purpose.

BACKGROUND

Scientific evidence has accumulated showing that prenatal and post natal early nutrition and other environmental factors cause programming of long-term health and well-being, and can impact the risk of developing chronic diseases. Several studies have shown that changes in dietary intake or manipulation of individual macro and micronutrients during the reproductive period can have an impact in several physiological processes, such as growth, metabolism, appetite, cardiovascular function among others (Koletzko B et al (2011) Am J Nutr 94(s):2036-43S). Therefore nutritional status (nutrient stores and dietary intake) of women before and during pregnancy is of relevance to optimize neonatal and child health outcomes. Maternal nutrition is thought to affect the availability and supply of nutrients to the developing fetus that are required for critical developmental processes.

Childhood overweight and obesity are major public health problem in a wide range of countries (including middle and low-income countries) and increasing rates of overweight and obesity have been reported in the last three decades. In 2008 in the UK about 30% of children 2-15 years old were overweight or obese. Evidence shows that weight at 5 years of age is good indicator of future health and well-being of a child (Gardner et al (2009) Pediatrics 123:e67-73). It has been shown that obesity in childhood increases the risk of adult obesity and other highly detrimental chronic conditions such as cardiovascular disease, type 2 diabetes, hepatic, renal and musculoskeletal complications, etc, among others. There is strong evidence that once obesity is established it is difficult to reverse through interventions and continues till adulthood (Waters E et al. (2011) Cochrane Database of Systematic Reviews 12), underlining the importance of childhood obesity prevention efforts.

Some possible early-life determinants including maternal obesity and diabetes, excess gestational weight gain, maternal smoking, rapid infant growth have been clearly associated with later in life overweight and obesity (Monasta L et al. (2010) Obesity Reviews. 11:695-708). Although the association may be modest for each of these factors, a large effect may be achieved when acting on a small attributable risk if the risk factor is highly prevalent in a population. Also some possible determinants may become more important than others because they are easier to be addressed through the implementation of an effective intervention.

Micronutrient deficiencies have profound and often persistent effects on fetal tissues and organs, even in the absence of clinical signs of their deficiency in the mother (Ashworth C J et al (2001) 122:527-35). Inadequate intakes of multiple micronutrients are common among women of reproductive age living in resource poor-settings (Torhem L E et al. (2010) J. Nutr. 140: 2051S-58S), and in some settings malnourishment related to overweight and obesity are also emerging concerns due to poor diet.

The inventors have investigated micronutrient deficiencies in women in order to identify micronutrients that can be used in prenatal and post natal early nutrition to program long-term health and well-being, and that—in particular—have a positive impact on reducing the risk of developing chronic diseases, such as overweight obesity, excessive fat accumulation and associated metabolic disorders such as diabetes, cardiovascular diseases and hypertension.

Any reference to prior art documents in this specification is not to be considered an admission that such prior art is widely known or forms part of the common general knowledge in the field.

It would therefore be desirable to provide the art with a solution that allows it to reduce the likelihood of developing overweight, obesity, excessive fat accumulation and/or associated disorders as early in life as possible. It would be in particular useful if this solution allowed to target subjects which are at an increased risk of developing overweight, obesity, excessive fat accumulation and/or associated metabolic disorders.

One object of the present invention is hence to improve the state of the art and in particular to provide a solution that overcomes at least some of the disadvantages of the present state of the art and that satisfies the needs expressed above, or to at least provide a useful alternative.

SUMMARY

The invention relates to the use of vitamin B12 for use in the prevention of overweight, obesity, excessive fat accumulation and/or associated metabolic disorders in the offspring of overweight and/or obese mothers. The vitamin B12 is to be administered to women desiring to get pregnant and/or to the mother during pregnancy and/or lactation, in various forms.

DETAILED DESCRIPTION

The present inventors were surprised to see that they could achieve this objective by the subject matter of the independent claims. The dependent claims further develop the idea of the present invention.

The present inventors have investigated the role of epigenetics as a mediator and a marker of early nutritional effects on human childhood body composition and the risk of humans developing obesity and insulin-resistance related disorders later in life. They have conducted thorough and detailed analyses in multi-cohort studies and were surprised to find that overweight and/or obese expecting mothers have a more profound vitamin B12 deficiency than normal weight mothers which led to an increased likelihood that their offspring develops overweight, obesity, excessive fat accumulation and/or associated metabolic disorders.

Consequently, the present invention relates in part to vitamin B12 for use in the prevention of overweight, obesity, excessive fat accumulation and/or associated metabolic disorders in the offspring.

The present invention also relates to the use of vitamin B12 for the preparation of a composition for the prevention of overweight, obesity, excessive fat accumulation and/or associated metabolic disorders in the offspring. The use may be non-therapeutic use.

The present invention further relates to vitamin B12 for use in the reduction of the likelihood for the development of overweight, obesity, excessive fat accumulation and/or associated metabolic disorders in the offspring.

Alternatively, according to any embodiment of the invention as described herein, vitamin B12 or a composition comprising vitamin B12 is used to prevent or to reduce the likelihood for the development of overweight, obesity, associated metabolic disorders and/or excessive fat accumulation.

The vitamin B12 may be for example to be administered to the mother before pregnancy, during pregnancy and/or during lactation. The mother may be an overweight and/or obese mother, as the vitamin B12 supplementation was found to be in particular effective in preventing overweight, obesity, excessive fat accumulation and/or associated metabolic disorders in the offspring of overweight and/or obese mothers.

Vitamin B12 supplementation is in particular effective in mothers which have low levels of vitamin B12 and/or have insufficient vitamin B12 intake.

Vitamin B12 intake is considered insufficient if it is below the Recommended Dietary Allowance (RDA). The RDA is the daily dietary intake level of a nutrient considered sufficient to meet the requirements of 97.5% of healthy individuals in each life-stage and gender group. It is calculated based on the Estimated Average Requirements (EAR), which are expected to satisfy the needs of 50% of the people in that age group based on a review of the scientific literature.

For example, the Vitamin B12 intake of a pregnant woman may be considered insufficient if it is below 2.6 µg/day.

Presently, vitamin B12 supplementation is used in the art, e.g., for the treatments of cyanide poisoning or hereditary deficiency of transcobalamin II.

"Overweight" is defined for an adult human as having a BMI between 25 and 30.

"Body mass index" or "BMI" means the ratio of weight in kg divided by the height in meters, squared.

"Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

For children the BMI is plotted on a BMI vs. age growth chart (for either girls or boys) to obtain a percentile ranking. Percentiles are the most commonly used indicator to assess the size and growth patterns of individual children. The percentile indicates the relative position of the child's BMI among children of the same sex and age. Children are considered overweight if their BMI is located between the $85^{th}$ and $95^{th}$ percentile. Children are considered obese if their BMI is located on or above the $95^{th}$ percentile.

Metabolic disorders that are associated with overweight, obesity and/or excessive fat accumulation are similar and well known to skilled artisans. For example, these disorders include cardiovascular diseases such as coronary heart disease; insulin resistance; type 2 diabetes; hypertension; sleep apnea, respiratory problems and/or dyslipidemia; but also some cancers such as endometrial, breast, and/or colon cancer; stroke; liver and gallbladder disease; osteoarthritis; and/or gynecological problems.

As vitamin B12 may be administered to expecting mothers during pregnancy and/or to mothers during lactation it may for example be to be administered in the form of a maternal food composition.

Women's nutrient needs increase during pregnancy and lactation. If the increased nutrient needs are satisfied this protects maternal and infant health. Lactation is demanding on maternal stores of energy, protein, and other nutrients that need to be established, and replenished.

Maternal food compositions are food compositions designed to help meeting the specific nutritional requirements of women during pregnancy and lactation.

For example, such maternal food compositions may comprise sources of protein, iron, iodine, vitamin A, and/or folate.

The maternal food composition may have any form that is accepted by mothers as part of their diet or as nutritional supplement.

For example, the maternal food composition may be selected from the group consisting of a powdered nutritional composition to be reconstituted in milk or water, a nutritional formula, a cereal based-product, a drink, a bar, a nutritional supplement, a nutraceutical, a yogurt, a dairy based product, a food sprinkler, a pill or a tablet.

Currently, particularly well accepted by consumers are powdered nutritional compositions to be reconstituted in milk or water.

Also well accepted are nutritional supplements, for example in the form of a tablet. The supplement provides selected nutrients while not representing a significant portion of the overall nutritional needs of the subject and/or does not represent more than 0.1%, 1%, 5%, 10%, or 20% of the daily energy need of the subject Vitamin B12 may be used in any amount that is effective in achieving the objective of the present invention. Skilled artisans will be able to determine appropriate dosages. Typically, dosage will depend on age, size and health status of the mother, on her lifestyle as well as on her genetic heritage.

In the prophylactic applications of the present invention, Vitamin B12 is administered in an amount that is sufficient to at least partially reduce the risk of the development of overweight, obesity, excessive fat accumulation and/or associated metabolic disorders in the offspring. Such an amount is defined to be "a prophylactic effective dose". Hence, vitamin B12 may be administered in a prophylactic effective dose.

For example, the vitamin B12 is administered in an amount corresponding to 0.26-26 µg Vitamin B12/day, for example in an amount corresponding to 1-14 µg Vitamin B12/day.

For the purpose of the present invention it is preferred if Vitamin B12 is administered regularly, for example two times a day, daily, every two days, or weekly, for example.

The vitamin B12 may be provided as a sustained release formulation. This way, vitamin B12 can be consumed less frequently, while the body is still constantly supplied with sufficient Vitamin B12.

For example the vitamin B12 may be to be administered before pregnancy (pre-pregnancy), during part of or the whole pregnancy and/or during the breastfeeding period (lactation). In one embodiment vitamin B12 may be administered during pregnancy and/or during lactation.

In one embodiment the composition of the invention is administered pre-pregnancy, for example during the 1, 2, or 4 months preceding the pregnancy or desired pregnancy.

As the nutritional requirements increase in the second and particularly the third trimester of pregnancy, it may be preferred to administer Vitamin B12 regularly throughout the third trimester of pregnancy or throughout the second and third trimester of pregnancy.

For example, vitamin B12 may be to be administered daily. The regular administration of vitamin B12 may be continued for at least 4, at least 8, at least 12, at least 16, at least 20, at least 24, at least 28, at least 32, or at least 36 consecutive weeks during pregnancy and/or during lactation.

Vitamin B12 may be used in pure form or as a natural vitamin B12 source or an extract thereof.

Highly purified or synthetic vitamin B12 may be used. It is preferred if vitamin B12 is provided from natural sources or as a natural source.

For example, vitamin B12 may be provided from natural sources such as shellfish, fish, organ meat, such as liver, meat, poultry, eggs, milk, yoghurt, cheese, milk based products; or extracts and/or combinations thereof.

Vitamin B12 may be used as single active ingredient.

It may also be co-administered with one or more other compounds that are active in reducing the risk of developing overweight, obesity, excessive fat accumulation and/or associated metabolic disorders in the offspring if administered to the mother before pregnancy, during pregnancy and/or during lactation.

In accordance with the present invention, vitamin B12 may be used to prevent the generation of overweight, obesity, excessive fat accumulation and/or associated metabolic disorders in the offspring later in life, in particular in the offspring of overweight, obese women and/or women suffering from metabolic syndrome.

"Later in life" includes childhood and adulthood. For example, "later in life" may refer to childhood, such as to an age of at least 3 years, for example at least 4 years or at least 6 years.

The inventors have found that the subject matter of the present invention allows it in particular to prevent overweight and/or obesity by reducing and/or avoiding the excessive build-up of fat mass in the offspring, for example abdominal and/or visceral fat mass.

This is advantageous as abdominal fat is particularly strongly correlated with cardiovascular diseases as well as other metabolic and vascular diseases, such as type 2 diabetes. Visceral fat, also known as intra-abdominal fat, is located inside the peritoneal cavity, between internal organs and torso and is also strongly correlated with type 2 diabetes.

It may be preferred to administer vitamin B12 in accordance with the present invention to mothers and/or expecting mothers whose children are particularly at risk of developing of overweight, obesity, excessive fat accumulation and/or associated metabolic disorders.

The studies leading to the present invention have shown that these may be for example overweight and/or obese mothers, and/or multiparous mothers.

Parity is a term that refers to the number of times a female has given birth to a baby. A woman who has given birth two or more times is multiparous.

The present invention also relates to a maternal food composition that can be used for the purpose of the present invention.

Consequently, the present invention relates to a maternal food composition, wherein the maternal food composition is a powdered nutritional formula comprising a protein source, a carbohydrate source, a lipid source, lecithin, preferably soya lecithin, a bulking agent and 0.37-18.2 µg vitamin B12/100 g dry weight.

The protein source may be dried milk or dried skimmed milk. As carbohydrate source sucrose and/or maltodextrin may be used. The lipid source may be vegetable oil. Vitamins and minerals may also be added. For example, vitamins and minerals may be added in accordance with the recommendations of Government bodies such as the USRDA. For example, the composition may contain per daily dose one or more of the following micronutrients in the ranges given: 100 to 2500 mg calcium, 35 to 350 mg magnesium, 70 to 3500 mg phosphorus, 2.7 to 45 mg iron, 1.1 to 40 mg zinc, 0.1 to 10 mg copper, 22 to 1,100 µg iodine, 6 to 400 µg selenium, 77 to 3000 µg of vitamin A or retinol activity equivalent (RAE), 8.5 to 850 mg Vitamin C, 0.14 to 14 mg Vitamin 131, 0.14 to 14 mg Vitamin B2, 1.8 to 35 mg niacin, 0.19 to 19 µg Vitamin B6, 60 to 1000 µg folic acid, 3 to 300 µg biotin, 1.5 to 100 µg Vitamin D, 1.9 to 109 µg Vitamin E.

The formulation may also alternatively or additionally contain glucose syrup, milk fat, fish oil, magnesium citrate, choline salts and esters, probiotic cultures, prebiotic fibers, and/or ascorbyl palmitate.

Flavor compounds, such as cocoa powder or honey, for example, may be added to provide taste variations.

The composition may further contain probiotic bacteria, folic acid, calcium, iron, ARA, EPA and/or DHA.

Those skilled in the art will understand that they can freely combine all features of the present invention described herein, without departing from the scope of the invention as disclosed. In particular, features described for the uses of the present invention may be applied to the maternal food composition of the present invention and vice versa.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification. Further advantages and features of the present invention are apparent from the figures and non-limiting examples.

BRIEF DESCRIPTION OF THE DRAWING

FIG. 1 shows that women presenting vitamin B12 deficiency (serum levels <200 ng/L) in late pregnancy deliver offspring with greater child's adiposity at ages 4 and 6 years measured by dual X-ray absorptiometry (DXA). In panel a) maternal vitamin B12 deficiency was significantly associated to the % of fat mass in the offspring at 4 years and b) a trend was observed for the % of fat mass in the offspring at 6 years.

EXAMPLES

Experimental and clinical research suggests that maternal nutritional state during pregnancy has lifelong effects in later in life outcomes in the offspring. In our work we sought to identify clinically and nutritionally defined groups whose offspring were at increased risk of later suboptimal body composition.

Study Design:

Mother-infant cohort included in the analysis:

501 Southampton Women's Survey (SWS) mother-infant pairs were selected as those with a late pregnancy maternal serum aliquot together with DXA measurements of body composition of the offspring at age 4 and 6 years. Summary characteristics of the SWS subjects analyzed were the following:

|  | Number | Percentage |
| --- | --- | --- |
| Parity | | |
| Primiparous | 244 | 48.7% |
| Multiparous | 257 | 51.3% |
| Maternal Age (years) | | |
| <25 | 34 | 6.8% |
| 25-35 | 398 | 79.4% |
| >35 | 69 | 13.8% |
| Ethnicity | | |
| White Caucasian | 486 | 97.0% |
| Non-white Caucasian | 15 | 3.0% |
| Maternal Pre-pregnant BMI | | |
| <20 kg/m2 | 32 | 6.5% |
| 20 kg/m2 | 464 | 93.5% |

1) Measurements of Vitamin B12 in Maternal Serum Samples

Vitamin B12 was analysed by automated immunoassay, using 'Access Immunoassay systems' on the Beckman Coulter DXi 800, a continuous, random access analyser. [Badióu S, Bariolet S, Laurens C, Aillaud N, Bargnoux A S, Mariano-Goulart D, Dupuy A M, Cristol J P. Comparison of isotopic and immunoenzymatic methods for folate and vitamin B12 determination. Clin Lab. 2010; 56:547-52.] The Access Vitamin B12 assay is a paramagnetic particle, chemiluminescent immunoassay for the quantitative determination of vitamin B12 levels in human serum and plasma (heparin) using the Access Immunoassay Systems (Beckman Dxl 800). The Access Vitamin B12 assay is a competitive binding immunoenzymatic assay which exhibits total imprecision of <12% across the assay range. The lowest detectable level of Vitamin B12 distinguishable from zero with 95% confidence is 50 pg/mL (37 pmol/L).

Quality control data (2 machines) are shown in the table below:

|  | Level 1 | Level 2 | Level 3 |
| --- | --- | --- | --- |
| Mean | 107.5/98.7 | 555.1/527.8 | 1093.4/1080.0 |
| SD | 9.65/12.2 | 42.4/34.9 | 107.1/126.4 |
| CV % | 9.65/12.35 | 6.29/8.04 | 9.79/11.70 |

The recommended cut-offs for diagnosing vitamin B12 deficiency and depletion are <148 pmol (<200 pg/ml) and <221 pmol/l (<300 pg/ml), respectively, in plasma or serum [Simpson J L, Bailey L B, Pietrzik K, Shane B, Holzgreve W. Micronutrients and women of reproductive potential: required dietary intake and consequences of dietary deficiency or excess. Part I-Folate, Vitamin B12, Vitamin B6. J Matern Fetal Neonatal Med. 2010 December; 23(12):1323-43; Institute of Medicine and Committee (IOM). Dietary reference intake: folate, other B vitamins and choline. Washington, D.C.: National Academy Press; 199.8].

For the analyses a level of serum B12<200 pg/ml or ng/L was used to indicate deficient B12 status.

2) Statistical Analyses to Uncover the Associations of the Deficiencies to Childhood Adiposity in SWS.

All SWS children's fat mass variables were positively skewed and were transformed with the use of Fisher-Yates normal scores to a normally distributed variable with a mean of 0 and an SD of 1 [Armitage P, Berry G. Statistical methods in medical research. Oxford, United Kingdom: Blackwell Science Ltd, 2002.]. Linear regression models were fitted with body-composition variables as the outcomes and with maternal micronutrient status as the predictor, taking account of potential confounding influences. Owing to sex differences in the children's body composition, all analyses were adjusted for the sex of the child, together with the child's age. Statistical analysis was performed with the use of Stata 11.1 [StataCorp. Stata: release 11. Statistical software. College Station, Tex.: StataCorp LP, 2009.] Thresholds for the statistical analysis of micronutrient deficiency/insufficiency are described in the text above.

Results:

The results of vitamin B12 in serum samples indicate that vitamin B12 deficiency is extremely prevalent in late gestation pregnant women in Southampton; a total 64.5% of the 501 subjects had serum vitamin B12 levels<200 ng/L.

Maternal vitamin B12 deficiency in late pregnancy was associated with greater offspring fat mass measured by DXA at age 4 years and showed a trend at 6 years.

TABLE 1

Child's adiposity by maternal vitamin B12 status.

| | DXA results | Vitamin B12 levels | | |
| --- | --- | --- | --- | --- |
| Age at measurement | Fat content | <200 ng/L | ≥20 ng/L | P-value |
| 4 yrs old | Percentage | 29.0 (212) | 27.9 (117) | 0.046 |
| 6 yrs old | Percentage (log-transformed) | 3.24 (308) | 3.21 (174) | 0.124 |

The results shown in Table 1 correspond to the log-transformed values used for the statistical analysis of the measures plotted in FIG. 1. Fat content percentage at age 4 years distribution was not skewed so it was not log-transformed.

Mean serum levels of Vitamin B12 showed significant differences according to pre-pregnancy BMI (Table 2) and obese mothers were identified at higher risk of maternal vitamin B12 deficiency (Table 3).

TABLE 2

Vitamin B12 status according to pre-pregnancy BMI.

| Pre-pregnancy BMI | Mean serum vitamin B12 levels (ng/L) |
|---|---|
| <18.5 | 197.3 |
| 18.5-25 | 170.2 |
| 25-30 | 164.3 |
| >30 | 143.7 |
| p-value (from ANOVA) | 0.009** |

TABLE 3

Increased risk of vitamin B12 deficiency according to pre-pregnancy BMI.

| Pre-pregnancy BMI | Odds ratio | 95% CI | P value |
|---|---|---|---|
| <18.5 | 0.61 | 0.04, 9.92 | 0.73 |
| 18.5-25 | Referent | | |
| 25-30 | 1.09 | 0.72, 1.66 | 0.67 |
| >30 | 2.36 | 1.23, 4.55 | 0.01** |

These results support that vitamin B12 deficiency has lasting effects on the offspring's risk of obesity and that obese mothers are at higher risk, and provide strong support for intervening in obese mothers before pregnancy, during pregnancy and during lactation to improve maternal vitamin B12 status.

The invention is claimed as follows:

1. A maternal food composition comprising a protein source, a carbohydrate source, a lipid source, lecithin, bulking agents, probiotic bacteria, and 0.18-18.2 μg vitamin B12/100 g dry weight of the maternal food composition.

2. The maternal food composition of claim 1, further comprising at least one component selected from the group consisting of folic acid, calcium, iron, arachidonic acid (ARA), eicosapentaenoic acid (EPA) and docosahexaenoic acid (DHA).

3. The maternal food composition of claim 1, wherein the maternal food composition is selected from the group consisting of a powdered nutritional composition to be reconstituted in milk or water, a nutritional formula, a cereal-based product, a drink, a bar, a nutritional supplement, a nutraceutical, a yogurt, a dairy based product, a food sprinkler, a pill and a tablet.

4. The maternal food composition of claim 1, comprising a natural source that provides at least a portion of the vitamin B12.

5. The maternal food composition of claim 1, formulated for administration to an overweight and/or obese mother before pregnancy, during pregnancy and/or during lactation.

* * * * *